US008071718B2

(12) United States Patent
Padilla De Jesus et al.

(10) Patent No.: US 8,071,718 B2
(45) Date of Patent: Dec. 6, 2011

(54) SELECTIVE RADIOLABELING OF BIOMOLECULES

(75) Inventors: Omayra Liz Padilla De Jesus, Clifton Park, NY (US); Ernest William Kovacs, Albany, NY (US); Matthias Eberhard Glaser, London (GB); Erik Arstad, London (GB); Faisal Ahmed Syud, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 794 days.

(21) Appl. No.: 11/961,108

(22) Filed: Dec. 20, 2007

(65) Prior Publication Data

US 2008/0161537 A1 Jul. 3, 2008

Related U.S. Application Data

(63) Continuation-in-part of application No. PCT/GB2005/004729, filed on Dec. 9, 2005.

(51) Int. Cl.
*A61K 38/00* (2006.01)
*A61K 51/00* (2006.01)

(52) U.S. Cl. .................. 530/345; 514/1.1; 424/1.69
(58) Field of Classification Search .................. None
See application file for complete search history.

(56) References Cited

U.S. PATENT DOCUMENTS

| 7,902,332 B2 * | 3/2011 | De Jesus et al. ............ 530/345 |
| 2008/0139787 A1 * | 6/2008 | De Jesus et al. ............ 530/345 |

FOREIGN PATENT DOCUMENTS

| WO | WO9935499 | 7/1999 |
| WO | WO03101972 | 12/2003 |
| WO | WO2005087818 | 9/2005 |
| WO | WO2006005046 | 1/2006 |
| WO | WO2006012569 | 2/2006 |
| WO | WO2006067376 | 6/2006 |
| WO | WO2006116629 | 11/2006 |
| WO | WO2006116736 | 11/2006 |
| WO | WO2007011696 | 1/2007 |

OTHER PUBLICATIONS

Young Soo Chang, et al; Bioconjugate Chem., vol. 16, No. 5, pp. 1329-1333, 2005.*
Tatsushi Toyokuni, et al, Synthesis of a new heterobifunctional linker, N-[4-(aminooxy)butyl]maleimide, for facile access to a thiol-reactive 18F-labeling agent; Bioconjugate Chem., vol. 14, p. 1253-1259, 2003.*
Ramenda et al., Synthesis of 18F-labeled Neurotensin(8-13) via Copper-Mediated 1,3-Dipolar [3+2}Cycloaddition Reaction, Letters in Drug Design & Discovery, vol. 4, pp. 279-285, 2007.*
Burley, G.A., "Directed DNA Metallization", JACS Communications, J. Am. Chem. Soc, 2006, 128, 1398-1399.
Link, James et al., "Non-canonical Amino Acids in Protein Engineering", Current Opinion in Biotechology (2003), 14: 603-609.
Torne, C.W. et al., "Peptidotriazoles on Solid Phase: [1,2,3]-Triazoles by Regiospecific Copper(I)-Catalyzed 1,3-Catalyzed 1.3-Dipolar Cycloadditions of Terminal Alkynes to Azides", American Chemical Society, J. Org. Chem., 2002, 67, 3057-3064.
Manetsch, Roman et al., "In Situ Click Chemistry: Enzyme Inhibitors Made to Their Own Specifications", J. Amer. Chem. Soc.,, 2004, 126, 12809-1281i.
Speers, Anna et al., "Activity-Based Protein Profiling in Vivo Using a Copper(1)-Catalyzed Azide-Alkyne [3+2] Cycloaddition", J. Am. Chem. Soc., 2003, 125, 4686-4687.
Link, A. James et al., "Cell Surface Labeling of *Escherichia coli* Via Copper(1)-Catalyzed [3+2] Cycloaddition", Am. Chem Soc., 2003, 11164-11165.
Fazio, F. et al, "Synthesis of Sugar Arrays in Microtiter Plate", J. Am. Chem. Soc., 2002, 124, 14397-14402.
Mindt, Thomas et al., "Click to Chelate": Synthesis and Installation of Metal Chelates Into Biomolecules in a Single Step, J. Am. Chem. Soc., 2006, 128, 15096-15097.
Gupta, Sayan et al., "Accelerated Bioorthogonal Conjugation: A Practical Method for the Ligation of Diverse Functional Molecules to a Polyvalent Virus Scaffold", Bioconjigate Chem., 2005, 1572-1579.
Lewis, Warren et al., "Discovery and Characterization of Catalysts for Azide—Alkyne Cycloaddition by Fluorescence Quenching", J. Am. Chem. Soc., 2004, 126, 9152-9153.
Wang, Q. et al., "Bioconjugation by Copper(1)-Catalyzed Azide-Alkyne [3+2] Cycloaddition", J. Am. Soc., 2003, 125, 3192-3193.
Marik, Jan et al., "Click for PET: Rapid Preparation of [18F]fluoropeptides Using Cu Catalyzed 1,3-dipolar Cycloadditon", Tetrahedron Letters, 47, 2006, 6681-6684.
Hassane, Fatouma et al., "Targeted Liposomes: Convenient Coupling of Ligands to Preformed Vesicles Using 'Click Chemistry'", Bioconjugate Chem., 2006, 17, 849-854.
Agard, Nicholas et al., "A Comparative Study of Bioorthogonal Reactions with Azides", ACS Chemical Biology, 2006, vol. 1, No. 10, 644-648.
Hatzakis, Nikos et al., "Synthesis and Single Enzyme Activity of a Clicked Lipase-BSA Hetero-Dimer", Chem. Communications, 2006, 2012-2014.

(Continued)

*Primary Examiner* — Maury Audet
(74) *Attorney, Agent, or Firm* — Eileen B. Gallagher

(57) ABSTRACT

Provided herein are methods for introducing fluorine atom onto a biomolecule comprising: (i) providing a linker comprising a thiol-reactive terminus and an azido/alkyne-reactive terminus; (ii) reacting the thiol-reactive terminus of the linker with a biomolecule comprising at least one thiol group or a reactive derivative thereof; and (iii) subsequently reacting the azido/alkyne-reactive terminus of the linker with a fluorine-substituted azide or alkyne respectively. Also provided are compositions and method of synthesis of bifunctional linkers and bioconjugates as well as radio-diagnostic agents comprising fluorine-labeled biomolecules.

13 Claims, 5 Drawing Sheets

OTHER PUBLICATIONS

Fukukawa, K. et al., "Synthesis of PEGylated Star Microgel With Core Functionality for Click Chemistry by Nitroxide-Mediated Radical Polymerization", The 231st ACS National Meeting—Mar. 26-30, 2006, Abstract.

Kolb, H. et al., Application of Click Chemistry to the Development of COX-2 and CA-II Inhibitors, The 231st ACS National Meeting, Mar. 26-30, 2006, Abstract.

Li et al., "Click Chemistry for 18F-Labeling of RGD Peptides and microPET Imaging of Tumor Integrin $\alpha v \beta 3$ Expression", Bioconjugate Chem., vol. 18, No. 6, pp. 1987-1994, Noveber 1, 2007.

Hermanson et al., Bioconjugate Techniques, Academic Press, San Diego, US, pp. 146-152, section "Thiol-Reactive Chemical Reactions", XP002523340, 1996.

Cai et al., "A Thiol-Reactive 18F-Labeling Agent, N-[2-(4-18F-Fluorobenzamido)Ethyl]Maleimide, and Synthesis of RGD Peptide-Based Tracer for PET Imaging of $\alpha v \beta 3$ Integrin Expression", Journal of Nuclear Medicine, vol. 47, No. 7, pp. 1172-1180, Jul. 1, 2006, XP002470156.

PCT International Search Report dated May 6, 2009.

* cited by examiner

SELECTIVE RADIOLABELING OF BIOMOLECULES

CROSS-REFERENCE TO RELATED APPLICATIONS

This application is a continuation-in-part of PCT application PCT/GB2005/004729, filed on Dec. 9, 2005, entitled "Radiolabelling Methods," and U.S. application Ser. No. 11/606,898 entitled "Fluorine-Labeled Compounds" with a filing date of Nov. 30, 2006, both of which are incorporated herein by reference.

BACKGROUND

Methods to introduce fluorine atoms, particularly radioactive fluorine atoms onto biomolecules comprising amino acid residues are of considerable interest. However, since radioactive fluorine atoms, such as $^{18}F$, have a relatively short lifetime of about 110 minutes, time-efficient methods are required to introduce radiofluorine onto biomolecules.

There is a continuing need for efficient and site-specific methods for introducing fluorine atom(s) including radioactive fluorine atom(s) onto biomolecules.

BRIEF DESCRIPTION

In one aspect, methods for introducing fluorine atom onto a biomolecule, such as polypeptide are disclosed. The methods may comprise: (i) providing a linker comprising a thiol-reactive terminus and an azido/alkyne-reactive terminus; (ii) reacting the thiol-reactive terminus of the linker with a biomolecule including at least one thiol group or a reactive derivative thereof; and (iii) subsequently reacting the azido/alkyne-reactive terminus of the linker with a fluorine-substituted azide or alkyne respectively.

In another aspect, methods are provided for introducing one or more fluorine atoms onto a biomolecule. The methods comprises (i) reacting the thiol-reactive group of Mal-alkyne bifunctional linker, such as N-(but-3-ynyl)-3-(2,5-dioxo-2,5-dihydro-1H-pyrrol-1-yl)propanamide linker (1) with a biomolecule comprising at least one thiol group; and (ii) subsequently reacting the alkyne group of the linker with a fluorine-substituted azide.

In still another aspect, bioconjugates comprising structural units derived from (i) a biomolecule comprising at least one thiol group; and (ii) a linker; are provided. The linker may be prepared by a method comprising reacting an amine compound comprising an azido or alkyne-reactive functional group with a carboxylic acid or an activated ester comprising a thiol-reactive functional group. In another aspect the linker may be prepared by reacting an amine compound comprising a thiol-reactive functional group with a carboxylic acid or an activated ester compound comprising an azido or alkyne-reactive functional group.

In yet another aspect, bioconjugate made using the methods, linkers, and biomolecules are provided herein.

In another aspect, the compositions of linkers are provided.

FIGURES

These aspects, and advantages of the present invention will become better understood when the following detailed description is read with reference to the accompanying drawings in which like characters represent like parts throughout the drawings, wherein FIG. 1 shows HPLC analysis of a reaction mixture of the non-optimized system showing $^{18}F$ click labeled Anti-Her2 affibody (27) (a, radioactivity channel; b, UV channel at 280 nm).

Figure 5:
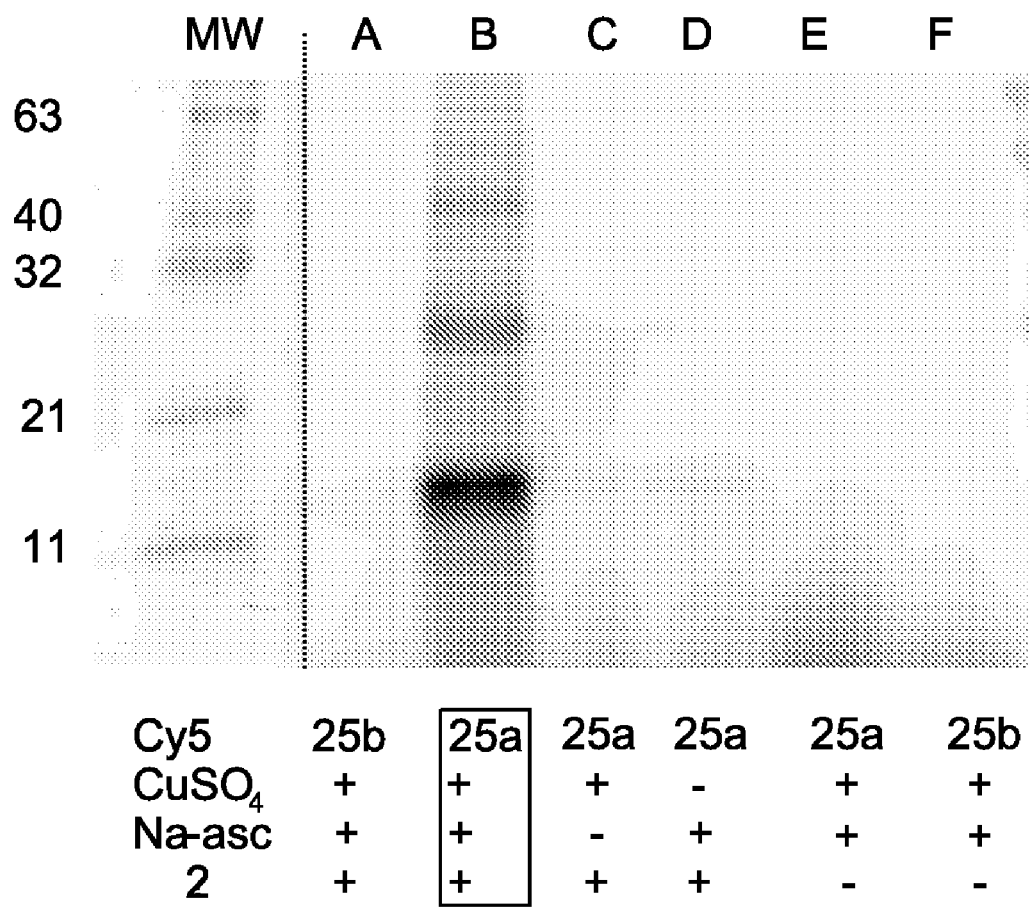

FIG. 5 shows the SDS-PAGE protein gel of a click conjugate between alkynylated affibody (22) and Cy5 labeled Azido PEG (25a). Fluorescence emission of Cy5 dye is observed at expected molecular weight of conjugate product (26) when in the presence of $Cu^I$ source and reducing reagent. No presence of conjugated product is observed in the absence of any of these in the control experiments.

DETAILED DESCRIPTION

The following detailed description is exemplary and not intended to limit the invention of the application and uses of the invention. Furthermore, there is no intention to be limited by any theory presented in the preceding background of the invention or the following detailed description.

To more clearly and concisely describe and point out the subject matter of the claimed invention, the following definitions are provided for specific terms that are used in the following description and the claims appended hereto. The singular forms "a", "an", and "the" include plural referents unless the context clearly dictates otherwise.

As used herein, the term "activating group" refers to any group that makes a carbonyl group more reactive towards nucleophiles, for example, N-hydroxysuccinimide, sulfo-N-hydroxysuccinimide, acid chloride, and urea intermediates.

As used herein, the term "azido-reactive terminus" and/or "azido-reactive functional group" refers to any functional group that can react with an azide functional group. Some examples of azido-reactive functional groups include, but are not limited to, alkynes, allenes and phosphines.

As used herein, the term "alkyne-reactive terminus" and/or "alkyne-reactive functional group" refers to any functional group that can react with an alkyne functional group. Examples of an alkyne-reactive functional group includes, but it is not limited to, azides, which can react in the presence of a source of $Cu^I$, including but not limited to, $Cu^0$, $Cu^I$, $Cu^{II}$, and a reducing reagent such as sodium ascorbate.

As used herein, the term "aliphatic radical" or "aliphatic group" generally refers to an array of carbon atoms that is not cyclic and has a point of attachment that is an $sp^3$ carbon atom. The array of carbon atoms may further comprise any combination of $sp^3$, $sp^2$, or sp hybridized carbon atoms. Further, the array of carbon atoms may be monovalent, divalent, or trivalent. Examples of alkyl groups include methyl, ethyl, n-propyl, isopropyl, n-butyl, tert-butyl, isooctyl, benzyl, cyclohexylmethyl, and phenethyl, 1',1'-dimethylbenzyl.

As used herein, the terms "aromatic radical" or/and "aromatic group" refers to a cyclic array of $sp^2$ hybridized carbon atoms and conjugated carbon-carbon double bonds, and has a point of attachment at an aromatic $sp^2$ hybridized carbon atom that forms part of the cyclic array of carbon atoms. The aromatic group or radical may have from one to the maximum permissible number of substituents. Examples of aryl groups include phenyl, substituted phenyl, tolyl, substituted tolyl, xylyl, mesityl, chlorophenyl, naphthyl, furyl, thienyl, and pyrrolyl.

As used herein, the term "cycloalkyl radical" or a "cycloalkyl group" refers to a cyclic array of $sp^3$ hybridized carbon atoms, and has a point of attachment at an $sp^3$ hybridized carbon atom that forms part of the cyclic array of carbon atoms. The array of carbon atoms may further comprise any combination of $sp^3$, $sp^2$, or sp hybridized carbon atoms. Further, the cyclic array of carbon atoms may be substituted with one to the maximum permissible number of substituents. Furthermore, the array of cyclic atoms may comprise heteroatoms, such as O, N, or S. Examples of cycloalkyl groups include cyclohexyl, methylcyclohexyl, trimethylcyclohexyl, phenylcyclohexyl, tetrahydropyranyl, 4-thiacyclohexyl, and cyclooctyl.

The term "a disulfide group capable of a thiol exchange reaction with a thiol group" refers to groups that may react with a thiol group of a biomolecule. Thus, a disulfide may be regarded as a thiol-reactive group. Pyridyl disulfide is an example of such a disulfide.

As used herein, the term "fluorine-substituted azide" denotes an azide-containing compound having at least one fluorine substituent. Further, the fluorine substituent may be of any isotopic variety, such as for example, $^{18}F$ and $^{19}F$. The azide may be an aliphatic azide, a cycloaliphatic azide, or an aromatic azide. Furthermore, the cycloaliphatic azides and aromatic azides may have monocyclic, bicyclic, or polycyclic structures.

As used herein, the term "fluorine-substituted alkyne" denotes an alkyne-containing compound having at least one fluorine substituent. Further, the fluorine substituent may be of any isotopic variety, such as for example, $^{18}F$ and $^{19}F$. The alkyne may be an aliphatic alkyne, a cycloaliphatic alkyne, or an aromatic alkyne. Furthermore, the cycloaliphatic alkynes and aromatic alkynes may have monocyclic, bicyclic, or polycyclic structures.

As used herein, the terms "protein", "peptide" and "polypeptide" are used herein to describe any chain of amino acids, regardless of length or post-translational modification such as glycosylation or phosphorylation. Thus, the terms may be used interchangeably herein to refer to a polymer of amino acid residues. The terms also apply to amino acid polymers in which one or more amino acid residue is an artificial chemical mimetic of a corresponding naturally occurring amino acid. Thus, the term "polypeptide" includes full-length, naturally occurring proteins as well as recombinantly or synthetically produced polypeptides that correspond to a full-length naturally occurring protein or to particular domains or portions of a naturally occurring protein.

The terms "radical" and "group", as applied to the terms "alkyl", "aliphatic", "cycloaliphatic", and "aromatic" are used interchangeably herein.

As used herein the term "thiol-reactive terminus" and/or "thiol-reactive functional group" refers to a functional group that may react with a thiol group or a mercaptan group (i.e., —SH group). Examples of thiol-reactive functional groups include, but are not limited to a maleimido group, a haloaliphatic group, a haloaromatic group, a halocycloaliphatic group, a (haloacetyl)alkyl group, a (haloacetyl) cycloalkyl group, a (haloacetyl)aryl group, an $\alpha,\beta$-unsaturated sulfone group, a vinyl sulfone group, an $\alpha,\beta$-unsaturated carbonyl group, an epoxy group, an aziridine group, and a disulfide group capable of a thiol exchange reaction with a thiol group.

Suitable maleimido groups include the parent (unsubstituted) group as well as derivatives comprising aliphatic, cycloaliphatic or aromatic groups as substituents. Suitable $\alpha,\beta$-unsaturated carbonyl groups include those comprising an acryloyl group. Suitable $\alpha,\beta$-unsaturated carbonyl groups include $\alpha,\beta$-unsaturated esters and $\alpha,\beta$-unsaturated sulfones. Vinyl sulfone group is a specific example of an $\alpha,\beta$-unsaturated sulfone group.

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Aspects of the invention relate to a method for introducing a fluorine atom onto a biomolecule. The method includes the steps of (i) providing a linker including a thiol-reactive terminus and an azido or an alkyne-reactive terminus;

(ii) reacting the thiol-reactive terminus of the linker with the biomolecule including at least one thiol group or a reactive derivative thereof; and (iii) subsequently reacting the azido or the alkyne-reactive terminus of the linker with a fluorine-substituted azide or alkyne group respectively.

Another aspect of the invention is to provide a bioconjugate composition comprising structural units derived from a biomolecule comprising at least one thiol group and a linker. The linker may be prepared by a method comprising reacting an amine compound comprising an azido or alkyne-reactive functional group with a carboxylic acid or an activated ester comprising a thiol-reactive functional group. In another aspect the linker may be prepared by reacting an amine compound comprising a thiol-reactive functional group with a carboxylic acid or an activated ester compound comprising an azido or alkyne-reactive functional group.

Biomolecules

As used herein, the term "biomolecules" refers to naturally occurring or engineered molecules that comprise at least one thiol group (also sometimes referred to as "mercapto" group) or a reactive derivative thereof for reaction with the linker. The thiol group may either occur naturally in the biomolecule or may be chemically introduced or engineered using standard biological methods or suitable art recognized methods. In some embodiments, the biomolecules specifically exclude having fewer than 50 amino acid residues.

Such biomolecules may either have one or more SH groups in their natural state, or they may be engineered, for example using standard molecular biology techniques. Examples of biomolecules having a SH group naturally include those linked to one or more cysteine amino acids. By the term "reactive derivative thereof" is meant a derivative of the SH group which is activated so as to generate the free thiol group for reaction with the linker compound.

Examples of biomolecules that comprise either one or more thiol groups naturally or chemically engineered thiol groups include peptides, polypeptides, vector, lipids, polysaccharides, glycosaminoglycans and modified versions thereof, glycolipids, glycoproteins, synthetic polymers, cell response modifiers, (e.g., growth factors, chemotactic factors, or cytokines), enzymes, receptors, neurotransmitters, hormones, cytokine, vaccines, haptens, toxins, interferons, and ribozymes. The disclosed methods may also be applied to molecules that do not contain a thiol group, but are conjugated to a molecule that does contain a thiol group. Further examples of biomolecules include proteins, protein fragments, protein variants, scaffold-based proteins, engineered proteins, nucleotides and related molecules, nucleic acids, oligo-DNA or oligo-RNA peptide conjugates, antibodies such as polyclonal and monoclonal antibodies, and antibody-based fragments. Thus, the disclosed methods may be used to fluorinate nucleic acids including deoxyribonucleic acids (e.g., oligodeoxynucleotides, nucleic acid probes, plasmids), ribonucleic acids (e.g., siRNA) associated with a thiol-containing molecule such as a polypeptide that has a thiol group.

The biomolecules may be any naturally occurring or engineered biomolecules having at least one thiol group. In all embodiments, the biomolecule may include naturally occurring and/or non-natural amino acid residues. In another embodiment, the biomolecule comprising the at least one thiol group comprises a cysteine residue or an unnatural group. By the term "cysteine residue" is meant the structural fragment other than the thiol group that results after cysteine is included as a part of the biomolecule chain. In still another embodiment, the biomolecule for reaction with the linker is one that has an engineered cysteine residue, which means that a suitable precursor biomolecule may be chemically modified to generate the desired biomolecule having the thiol group and the cysteine residue.

In some cases, a biomolecule may be treated with a reducing agent to generate a reactive thiol group. For example, a biomolecule having a disulfide linkage may be reduced with a suitable reducing agent to produce two equivalents of a biomolecule having a thiol group. Examples of useful reducing agents include 2-mercaptoethanol, 2-mercaptoethanolamine, dithiothreitol (DTT), and tris-(2-carboxyethyl)phosphine (TCEP).

Linkers:

As used herein, the term "linker" refers to a bi-functional compound comprising a thiol-reactive terminus or a protected derivative thereof, and an azido or alkyne-reactive terminus or a protected derivative thereof. The linkers may be used to attach a thiol-containing compound at one end via the thiol-reactive terminus, and for attachment to azide or alkyne, especially fluorine-substituted azide or alkyne at the other end via the azido or alkyne-reactive terminus respectively. As used herein, the term "Mal-alkyne bifunctional linker" refers to a linker having a maleimido group at a first terminal and an alkyne group at a second terminal, such as N-(but-3-ynyl)-3-(2,5-dioxo-2,5-dihydro-1H-pyrrol-1-yl)propanamide linker (1) and "Mal-azide bifunctional linker" refers to a linker having a maleimido group at a first terminal and an azide group at a second terminal, such as compound (2). Some non-limiting examples of linkers are shown in structures (1)-(6).

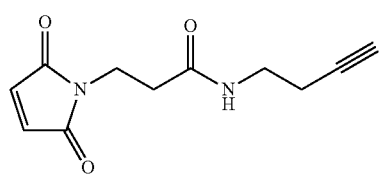

(1)

-continued

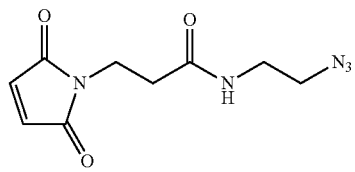

(2)

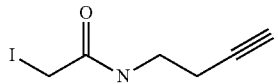

(3)

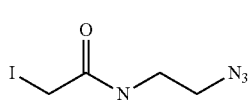

(4)

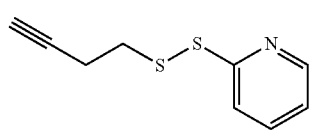

(5)

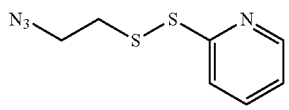

(6)

In some embodiments, the thiol-reactive terminus, the azido or alkyne-reactive terminus, or both the thiol-reactive terminus and the azido or alkyne-reactive terminus may be replaced with a precursor derivative. The linkers may be used to attach a thiol-containing compound at one end via the thiol-reactive terminus, and/or to attach azide or alkyne (e.g., fluorine-substituted azide or alkyne) at the other end via the azido or alkyne-reactive terminus respectively.

Linker Preparation

The linker may be prepared by any method that makes both the thiol-reactive functional group and the azido or alkyne-reactive functional group accessible for reaction with (i) the biomolecule having at least one thiol group, and (ii) the fluorine-substituted azide or alkyne, respectively. In one embodiment, the linker is prepared by reacting an amine compound comprising an azido or alkyne-reactive functional group with a carboxylic acid or an activated ester comprising a thiol-reactive functional group. Any amine compound having an azido or alkyne reactive functional group may be used. In an embodiment, the amine compound comprises a structure (7), $$G\text{-}J\text{-}NHR^1 \qquad (7)$$

wherein G is an azido or alkyne-reactive functional group, J is a linking unit, and $R^1$ is H, an aliphatic radical, an aromatic radical, or a cycloaliphatic radical. The nature of the divalent linking unit J may be designed to minimize steric hindrance, which could adversely affect the reactivity of the thiol-reactive and the azido or alkyne-reactive functional groups. One of the advantages of the present approach is that the linking unit may be tailored to alter the final properties of the bioconjugate. Thus, the linkers may vary in size, polarity, charge, and chemical composition to modify properties of the final conjugates, such as solubility and pharmacokinetics/pharmacodynamics (PK/PD) properties. Furthermore, the linkers may include additional handles for attachment of groups that would improve targeting and/or solubility.

In other embodiments, the linker may be prepared by reacting an amine compound comprising a thiol-reactive functional group with a carboxylic acid or an activated ester compound comprising an azido or alkyne-reactive functional group.

The carboxylic acid or activated ester comprises a structure (8),

L-M-COR²                                               (8)

wherein L comprises a thiol-reactive functional group, or a protected derivative thereof; M is a divalent linking unit, and $R^2$ is OH or an activating group. The activating group $R^2$ facilitates the reaction of the amine compound having the azido or alkyne-reactive functional group with the carbonyl carbon atom of structure (8).

In another embodiment, the linker composition comprising a formula:

L-M-CO—N(R¹)-J-G, wherein

L is a thiol-reactive functional group;

M and J are the bifunctional units/linking units;

$R^1$ is H, an aliphatic radical, an aromatic radical, or a cycloaliphatic radical; and G is an azido or alkyne-reactive functional group Exemplary synthetic approaches for preparing the linker having structure (1) and (2) are shown in Reaction Schemes 1 and 2.

Reaction Scheme 1

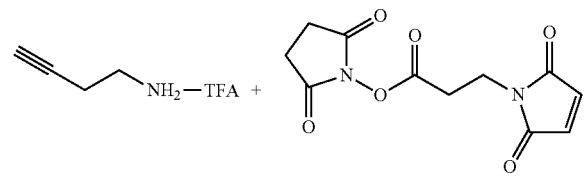

DMF/DIEA (1)

Reaction Scheme 2

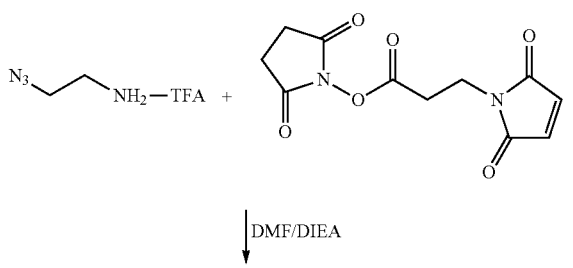

DMF/DIEA

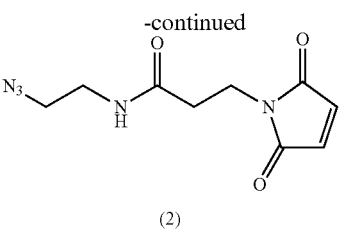

(2)

In Reaction Schemes 1 and 2, DMF stands for Dimethyl Formamide and DIEA stands for Di-isopropyl ethyl amine. Some examples of linkers that may be prepared using these methods are shown above in structures (1) to (6).

Bioconjugates

The products resulting from the reaction of the linker with the biomolecule having at least one thiol group is termed as a bioconjugate. Thus in an embodiment, the bioconjugate comprises structural units derived from: (i) a biomolecule comprising at least one thiol group; and (ii) a linker; where the linker is prepared by a method comprising reacting an amine compound comprising an azido or alkyne-reactive functional group with a carboxylic acid or an activated ester comprising an thiol-reactive functional group. In another embodiment, the bioconjugate comprises structural units derived from: (i) a biomolecule comprising at least one thiol group; and (ii) a linker; where the linker is prepared by a method comprising reacting an amine compound comprising a thiol-reactive functional group with a carboxylic acid or an activated ester comprising an azido or alkyne-reactive functional group. In another aspect the linker may be prepared by reacting an amine compound comprising a thiol-reactive functional group with a carboxylic acid or an activated ester compound comprising an azido or alkyne-reactive functional group.

Methods for Fluorinating Bioconjugates

The methods described herein enable the preparation of fluorine-labeled bioconjugates, more particularly radiofluorine (e.g., $^{18}F$) labeled bioconjugates. One of the advantages of these methods is that the linker may be attached selectively to a biomolecule such as a biomolecule under non-radioactive conditions in which the thiol group of the biomolecule may be reacted selectively with the thiol-reactive functional group of the linker, and the resulting bioconjugate may be purified prior to reaction with an $^{18}F$ or a normal fluorine-substituted azide or alkyne. Another advantage is that the radiofluorine label may be added selectively in a final step, eliminating the need for time consuming additional purification steps before the preparation of the final bioconjugate, especially at tracer levels.

The methods described herein for introducing fluorine onto a bioconjugate may be used to generate fluorinated bioconjugate of any length. Thus, in some embodiments the biomolecule of the bioconjugate comprises at least 50 amino acid residues or at least 100 amino acid residues.

In one aspect, methods for introducing one or more fluorine atom(s) onto a biomolecule are disclosed. The methods may comprise: (i) providing a linker comprising a thiol-reactive terminus and an azido or alkyne-reactive terminus; (ii) reacting the thiol-reactive terminus of the linker with a biomolecule comprising at least one thiol group or a reactive derivative thereof; and (iii) subsequently reacting the azido or alkyne-reactive terminus of the linker with a fluorine-substituted azide or alkyne respectively.

In some embodiments of the methods for introducing the fluorine atom onto the biomolecule, such as polypeptide, the thiol-reactive terminus of the linker is selected from a maleimido group, a haloaliphatic group, a haloaromatic group, a halocycloaliphatic group, a (haloacetyl)alkyl group, a (haloacetyl)cycloalkyl group, a (haloacetyl)aryl group, a vinyl sulfone group, an acryloyl group, an epoxy group, an aziridine group, and a disulfide group capable of a thiol exchange reaction with a thiol group.

More specifically, the methods described herein may be employed to introduce one or more fluorine atoms onto a biomolecule using Mal-alkyne bifunctional linker such as N-(but-3-ynyl)-3-(2,5-dioxo-2,5-dihydro-1H-pyrrol-1-yl) propanamide (1) as the linker. Such methods comprise: (i) reacting the thiol-reactive group of N-(but-3-ynyl)-3-(2,5-dioxo-2,5-dihydro-1H-pyrrol-1-yl)propanamide (1) with a biomolecule comprising at least one thiol group; and (ii) subsequently reacting the alkyne group of the intermediate product resulting from step (i) with a fluorine-substituted azide. In another embodiment, the methods may be employed to introduce one or more fluorine atoms onto a biomolecule using Mal-azide bifunctional linker such as compound (2) as the linker. Such methods comprise: (i) reacting the thiol-reactive functional group of compound (2) with a biomolecule comprising at least one thiol group; and (ii) subsequently reacting the azide group of the intermediate product resulting from step (i) with a fluorine-substituted alkyne.

The reaction of the azido or alkyne-reactive terminus of the linker with the fluorine-substituted azide or alkyne may be carried out in any medium that may range from mildly acidic to mild basic conditions. In an embodiment, the reaction may be conducted in a medium having a pH in a range from about 6 to about 9; and in another embodiment, in a pH range from about 7 to about 8. The reaction temperature may be varied from ambient temperature to about 70° C. Reaction time may vary, but generally may be from about 10 minutes to about 60 minutes. In some embodiments, the reaction time varies from about 10 minutes to about 30 minutes. However, longer reaction times may also be employed. The reaction may be carried out in the presence of $Cu^I$, or precursor thereof, including but not limited to $Cu^o$, $Cu^I$, or $Cu^{II}$ salts, in the presence of a reducing reagent, such as but not limited to, sodium ascorbate. Reaction Schemes 3 and 4 show possible approaches to prepare the fluorine labeled bioconjugates (9) and (10).

Reaction Scheme 3

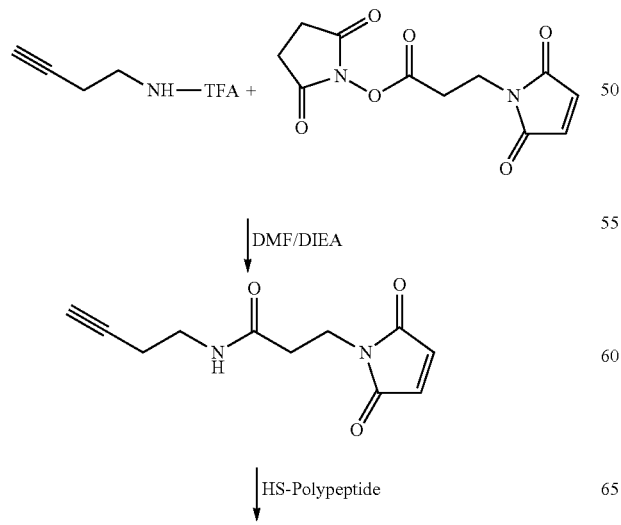

-continued

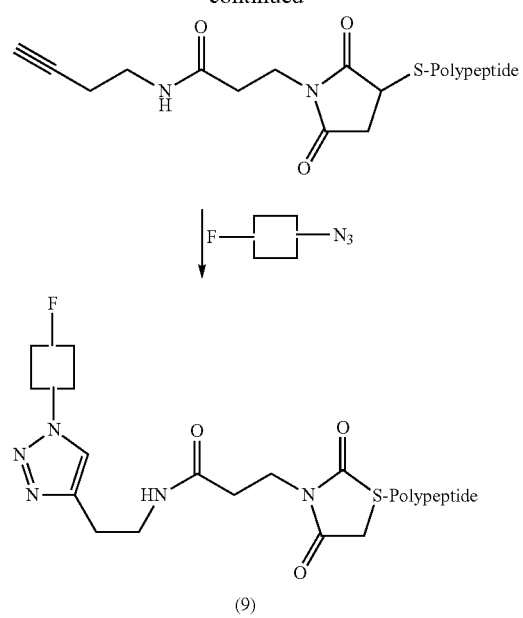

(9)

Reaction Scheme 4

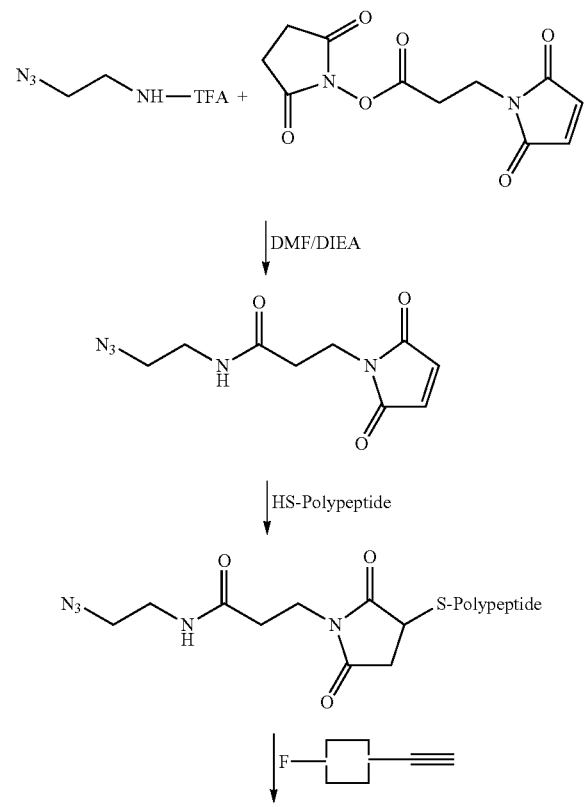

-continued

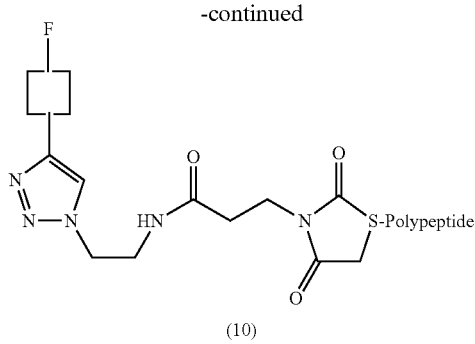

(10)

In one approach, the precursor to an alkyne or azide containing linker may be first reacted with a polypeptide comprising a thiol group and the resulting intermediate is transformed to give the desired bioconjugate. Alternatively, the precursor to an alkyne or azide containing linker may be first transformed to give the linker, which may then be reacted with the polypeptide comprising the thiol group to give product.

Using the above-described techniques, one may introduce fluorine or radiofluorine atom(s), such as $^{18}F$, onto a biomolecule When a fluorine-substituted azide or alkyne is reacted with a bioconjugate, a fluorine-substituted bioconjugate results. When a radiofluorine-substituted azide or alkyne is reacted with bioconjugate, a radiofluorine-labeled bioconjugate results. Non-limiting example of suitable fluorine-substituted azide/alkyne are shown in structures (11)-(14).

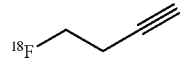

(11)

(12)

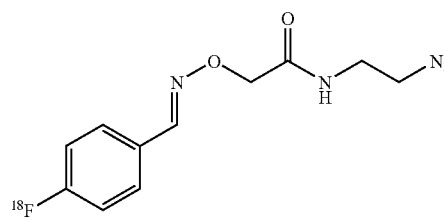

(13)

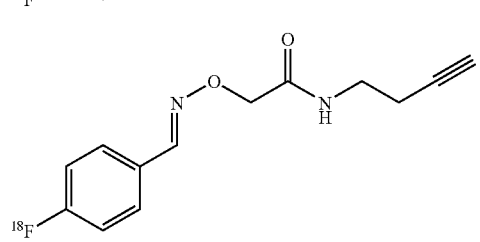

(14)

Any of the biomolecules, such as polypeptides, described previously having at least one thiol group may be used for preparing the bioconjugates. Biomolecules such as polypeptide, vectors, scaffold-based proteins and engineered binding proteins having at least one thiol group are especially valuable since such materials have potentially valuable diagnostic and therapeutic value. Thus in an embodiment, bioconjugates may be produced by reacting scaffold-based proteins such as affibodies with a Mal-alkyne bifunctional linker such as N-(but-3-ynyl)-3-(2,5-dioxo-2,5-dihydro-1H-pyrrol-1-yl) propanamide linker (1). In another embodiment, bioconjugates may be produced by reacting scaffold-based proteins such as affibodies with a Mal-azide bifunctional linker such as compound (2). Further, valuable fluorine-labeled bioconjugates may be produced by reacting the bioconjugate with a fluorine-substituted azide or alkyne.

The fluorine-labeled bioconjugates are valuable materials in diagnostic applications. $^{18}F$ labeled bioconjugates may be visualized using imaging techniques known in the art, such as for example PET (Positron Emission Tomography) and SPECT (Single Photon Emission Computed Tomography) techniques.

While only certain features of the invention have been illustrated and described herein, many modifications and changes will occur to those skilled in the art. It is, therefore, to be understood that the appended claims are intended to cover all such modifications and changes as fall within the true spirit of the invention.

EXAMPLES

Practice of the invention will be still more fully understood from the following examples, which are presented herein for illustration only and should not be construed as limiting the invention in any way.

The abbreviations used in the Examples section are expanded as follows: "mg": milligrams; "mL": milliliters; "mg/mL": milligrams per milliliter; "mmol": millimoles; "μL": microliter; "KDa": kilodaltons; "MALDI-MS": Matrix Assisted Laser Desorption Ionization Mass Spectrometry; "HPLC": High Pressure Liquid Chromatography; "LC-MS" Liquid Chromatography Mass Spectrometry, "ESI-MS" Electrospray Ionization Mass Spectrometry, "MALDI-TOF MS" Matrix Assisted Laser Desorption Ionization Time Of Flight Mass Spectrometry, "TFA": Trifluoroacetic acid; "DMSO": Dimethylsulfoxide; "DTT": dithiothrietol; "MeCN" acetonitrile, "PBS": phosphate buffered saline, "Mal": Maleimido; "ppm" parts per million, "MWCO: Molecular Weight Cut Off; "cold condition": without radioactive isotope and "radiochemical yield": fraction of activity originally present. Unless otherwise noted, all reagent-grade chemicals were used as received, and Millipore water was used in the preparation of all aqueous solutions.

Example 1

Preparation of 2-[$^{18}F$]Fluoroethylazide (11)

Reaction Scheme 5

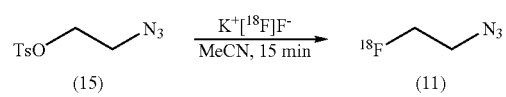

$[^{18}F]$-Fluoride was produced by a cyclotron using the $^{18}O$ (p,n)$^{18}F$ nuclear reaction with 19 MeV proton irradiation of an enriched [O]H$_2$O target. After the irradiation, a mixture of Kryptofix® (5 mg, 13.3 μmol), potassium carbonate (1 mg, 7.2 μmol), and MeCN (1 mL) was added to $^{18}F$-water (1 mL). The solvent was removed by heating at 80° C. under a stream of nitrogen (100 mL/min). Afterwards, MeCN (0.5 mL) was added and evaporated under heating and nitrogen stream. This procedure was repeated twice. After cooling to room temperature, a solution of toluenesulfonic acid-2-azidoethylester (15) in anhydrous MeCN (0.2 mL) was added. The reaction mixture was stirred for 15 min at 80° C. After addition of MeCN (0.3 mL), 2-[$^{18}$F]Fluoroethylazide (11) was distilled at 130° C. under a flow of nitrogen (15 mL/min) into a trapping vial containing MeCN (0.1 mL). This compound (11) was collected with a decay-corrected radiochemical yield of 54% (ref. to $^{18}$F-fluoride) and 63% distillation efficiency.

Figure 2:
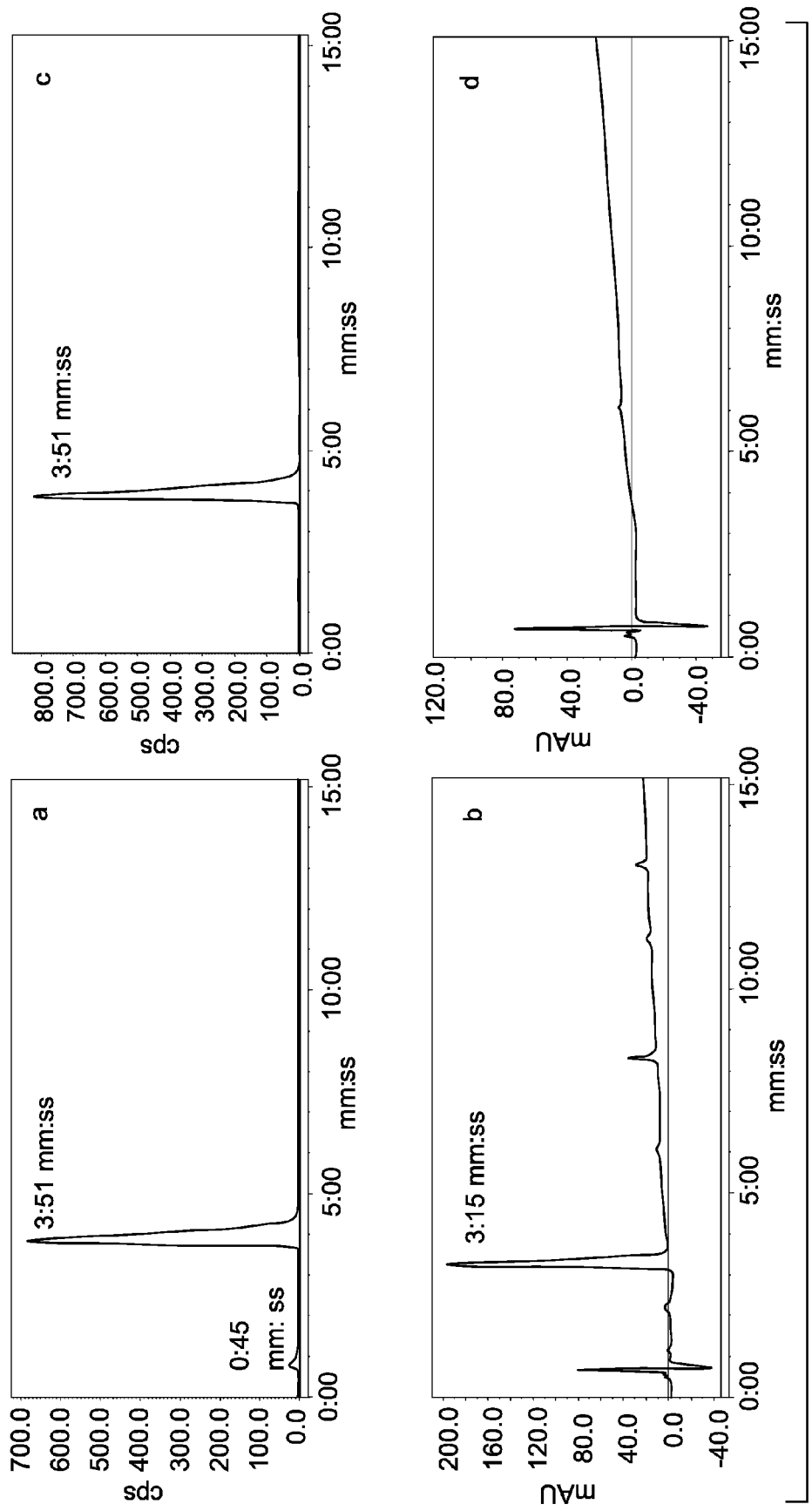
FIG. 2 shows HPLC analysis of a reaction mixture containing 2-[$^{18}F$]Fluoroethylazide (11) using gradient I, UV at 216 nm (a, radioactivity channel, 2-[$^{18}F$]Fluoroethylazide (11) at 3:51 min; b, UV channel). The distilled product shows only the presence of 2-[$^{18}F$]Fluoroethylazide (11) (c, radioactivity channel; d, UV channel).

FIG. 2 shows the results of the HPLC analysis of a reaction mixture containing 2-[$^{18}$F]Fluoroethylazide (11) using gradient I, UV at 216 nm (a, radioactivity channel, 2-[$^{18}$F]Fluoroethylazide (11) at 3:51 min; b, UV channel) and distilled product 2-[$^{18}$F]Fluoroethylazide (11) (c, radioactivity channel; d, UV channel).

Example 2

Concentration Studies Showing Triazole Formation at Different Concentrations of Small Substrate

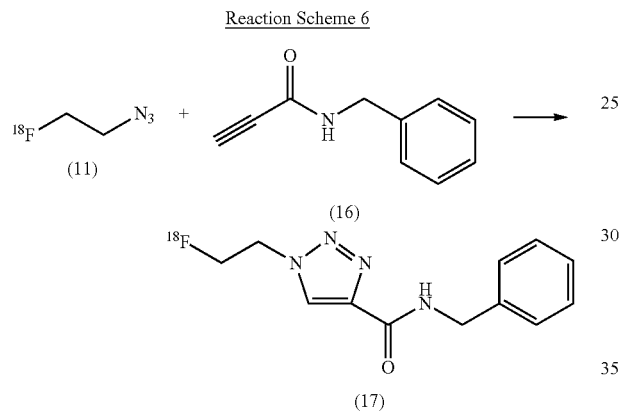

In the concentration study, alkyne model (16) (1.2-0.01 mg, 7.5-0.25 μmol) was dissolved in DMF (50 μL) and mixed under nitrogen with an aqueous solution of copper(II) sulfate (25 μl, 2.8 mg, 11.25 μmol), and sodium ascorbate (25 μL, 7.5 mg, 37.5 μmol). After addition of [$^{18}$F]2-fluoroethylazide (11) in MeCN (100 μl) and standing for 15 min. at room temperature, the mixture was analyzed by HPLC. The vials were subsequently heated (15 min, 80° C.) and again analyzed.

The resulting Triazole product (17) was obtained in quantitative yield at room temperature with a minimum alkyne model (16) concentration of 3.14 mM (100 μg). When the reaction mixture was heated at 80° C. the minimum alkyne model (16) concentration was 1.57 mM (50 μg) for a quantitative yield of resulting Triazole (17).

Figure 3:
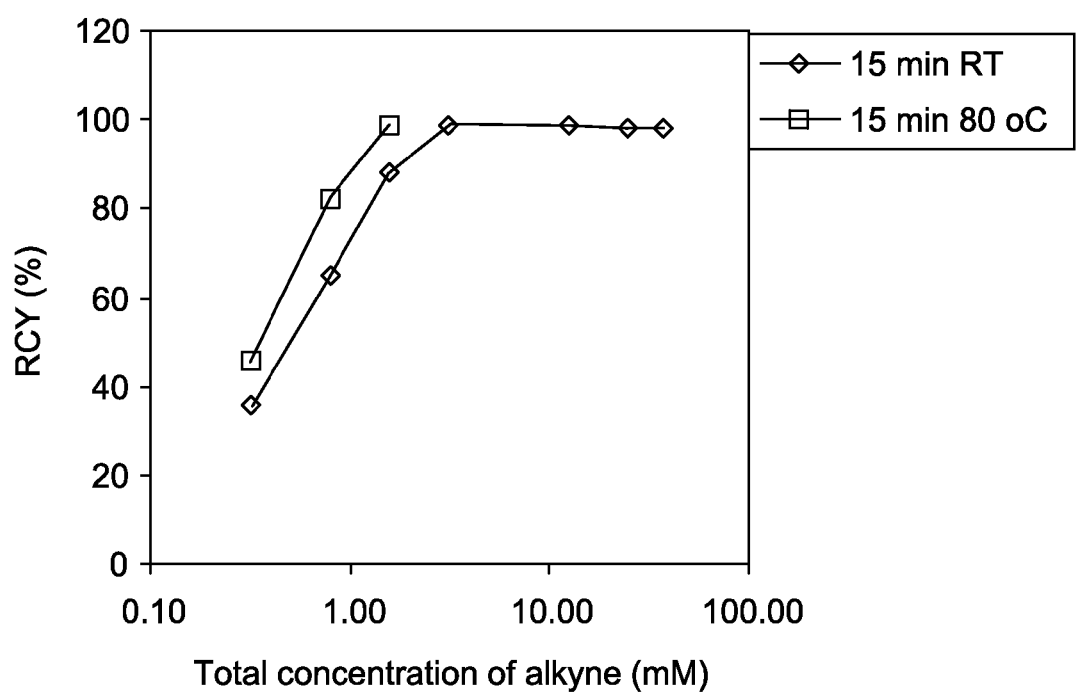
FIG. 3 shows the HPLC plot of radiochemical yield of triazole product (17) formed at different alkyne (16) concentrations and temperatures using model compound (16) and 2-[$^{18}F$]Fluoroethylazide (11).

FIG. 3 shows the HPLC plot of radiochemical yield of triazole product (17) formed at different alkyne (16) concentrations and temperatures using model compound (16) and 2-[$^{18}$F]Fluoroethylazide (11)

Example 3

Triazole Formation on Peptide

Preparation of [$^{18}$F](S)-6-Amino-2-(2-{(S)-2-[2-((S)-6-amino-2-{[4-(2-fluoro-ethyl)-[1,2,3]triazole-1-carbonyl]-amino}-hexanoylamino)-acetylamino]-3-phenyl-propionylamino}-acetylamino)-hexanoic acid (19)

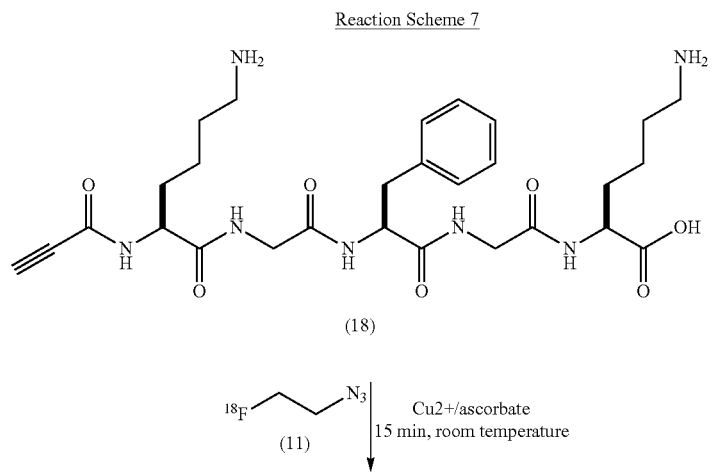

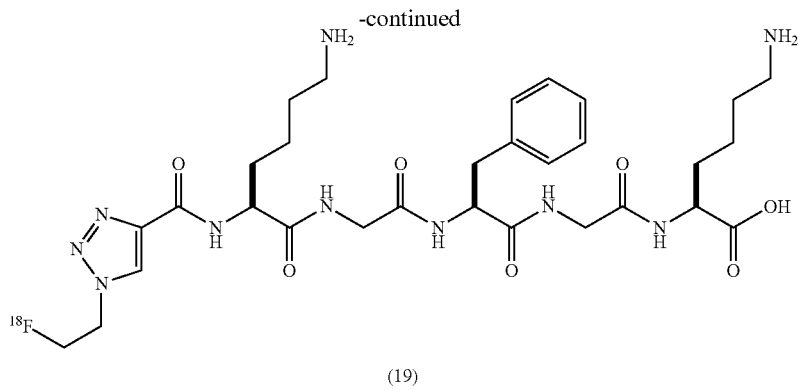

(19)

To a solution of copper(II) sulphate pentahydrate (4.3 mg, 17 μmol) in water (50 μL), was added sodium ascorbate (3.4 mg, 17 μmol) in water (50 μL) under nitrogen. After approximately one minute at room temperature, a solution of alkyne peptide precursor (18) was added (2 mg, 3.4 μmol, in sodium phosphate buffer, pH 6.0, 0.5 M, 50 μL), followed by a solution of 2-[$^{18}$F]Fluoroethylazide (11) (24-32 MBq) in MeCN (50 μL). The mixture was kept at room temperature for 15 minutes and diluted with HPLC mobile phase A (water, 0.1% TFA) (0.3 mL). The labeled peptide (19) was isolated using semi-preparative HPLC (UV at 216 nm, Rt=6:24).

Example 4

Synthesis of Mal-Alkyne Bifunctional Linker (1)

Reaction Scheme 8

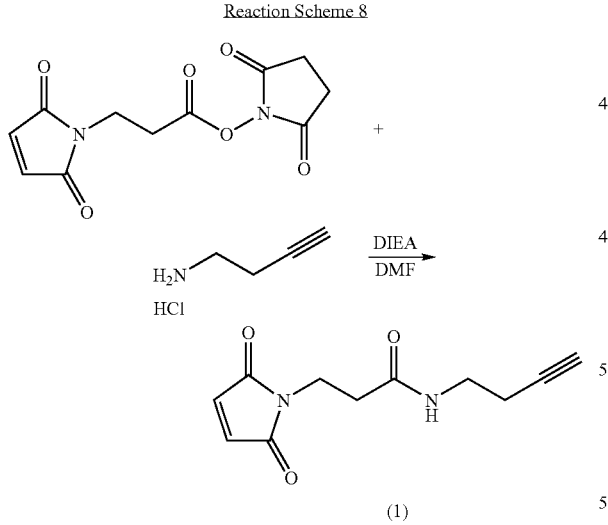

(1)

N-[β-Maleimidopropyloxy]succinimide ester (50 mg, 1.25 equiv) was dissolved in 1.0 mL of dry DMF. 3-Butyn-1-amine hydrochloride (16 mg, 1.0 equiv) was dissolved in 0.5 mL of dry dimethylformamide (DMF) and 26 μL of diisopropylethylamine (DIEA). This amine solution was added drop-wise to the succinimide ester while keeping the ester solution in an ice bath. The mixture was stirred at 0° C. for 10 min. The solution was warmed up to room temperature and stirred for 18 h. The solvents were evaporated under vacuum and the residue was dissolved in 5 mL CH$_2$Cl$_2$. The organic solution was extracted with brine (3×5 mL) and dried over MgSO$_4$. The solvent was removed under reduced pressure and the crude material was purified using flash chromatography (silica, MeOH/CH$_2$Cl$_2$). The product (1) was purified from grease by dissolving the sample in a minimum amount of CH$_2$Cl$_2$ (ca. 2 mL), followed by three washes with hexanes. The product (1) precipitated as a fluffy white solid. Characterization of the product was achieved using $^1$H-NMR. Yield: 8.2 mg (25%). $^1$H-NMR (500 MHz, CDCl$_3$): δ 2.02 (s, 1), 2.41 (t, J=5 Hz, 2), 2.57 (t, J=5 Hz, 2), 3.42 (td, J=5 Hz, 2), 3.88 (t, J=5 Hz), 5.90 (bs, 1), 6.73 (s, 2).

Example 5

Preparation of 2-Fluoroethyltriazole-Maleimide (Reference Compound) (21)

Reaction Scheme 9

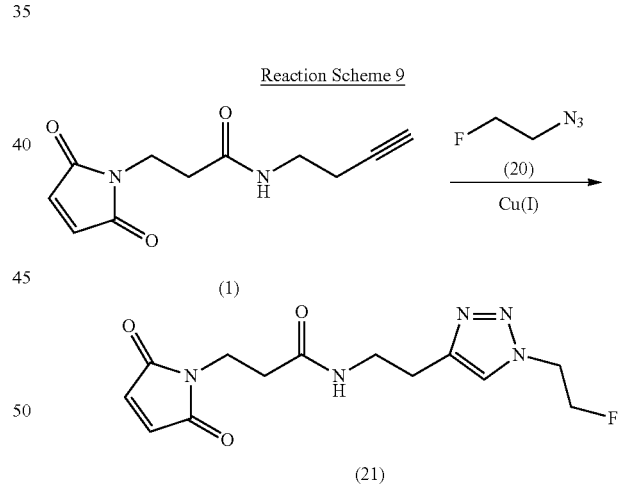

A mixture of sodium phosphate buffer (20 μl, 250 mM, pH 6.0), DMF (50 μl) and copper powder (100 mg, −40 mesh, Aldrich Cat. No. 26, 608-6) was purged with nitrogen gas (10 ml/min) for 5 minutes. After addition of 2-fluoroethylazide (20) (10 μmol) in DMF (9.2 μl, prepared as described by Glaser and Årstad 2007), and 3-(N-maleimidyl)-N-(3-propargyl) propionamide (1) (2.1 mg, 9.5 μmol) in DMF (20 μl), the vessel was stirred at room temperature for 1 hour. The solvent was removed under reduced pressure (1 mbar, 80° C.). Purification by preparative HPLC gave the fluoroethyl-triazole (21) compound (1.2 mg, 41%). HR ESI-MS: for C$_{13}$H$_{16}$N$_5$O$_3$F (Calculated. m/z=310.1310. Found m/z=310.1314).

Purification by preparative HPLC (gradient: 5-80% solvent B over 15 min where A=H₂O/0.1% TFA and B=MeCN/0.1% TFA, flow rate: 15 mL/min; column: Luna 5 μm C18(2) (Phenomenex), 75×30 mm, detection: UV 216 nm.

Example 6

Affibody Alkynylation and Reaction with Mal-Alkyne Bifunctional Linker

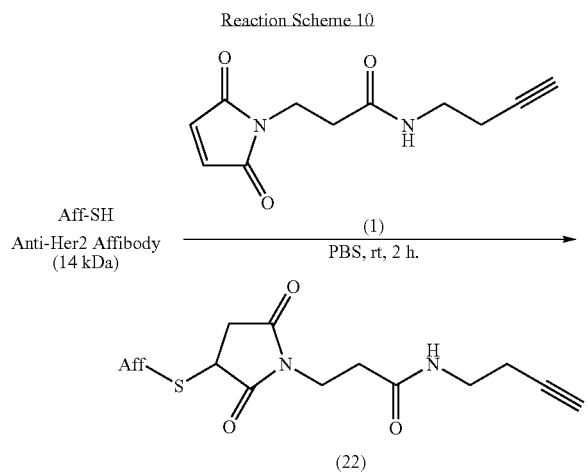

Figure 4:
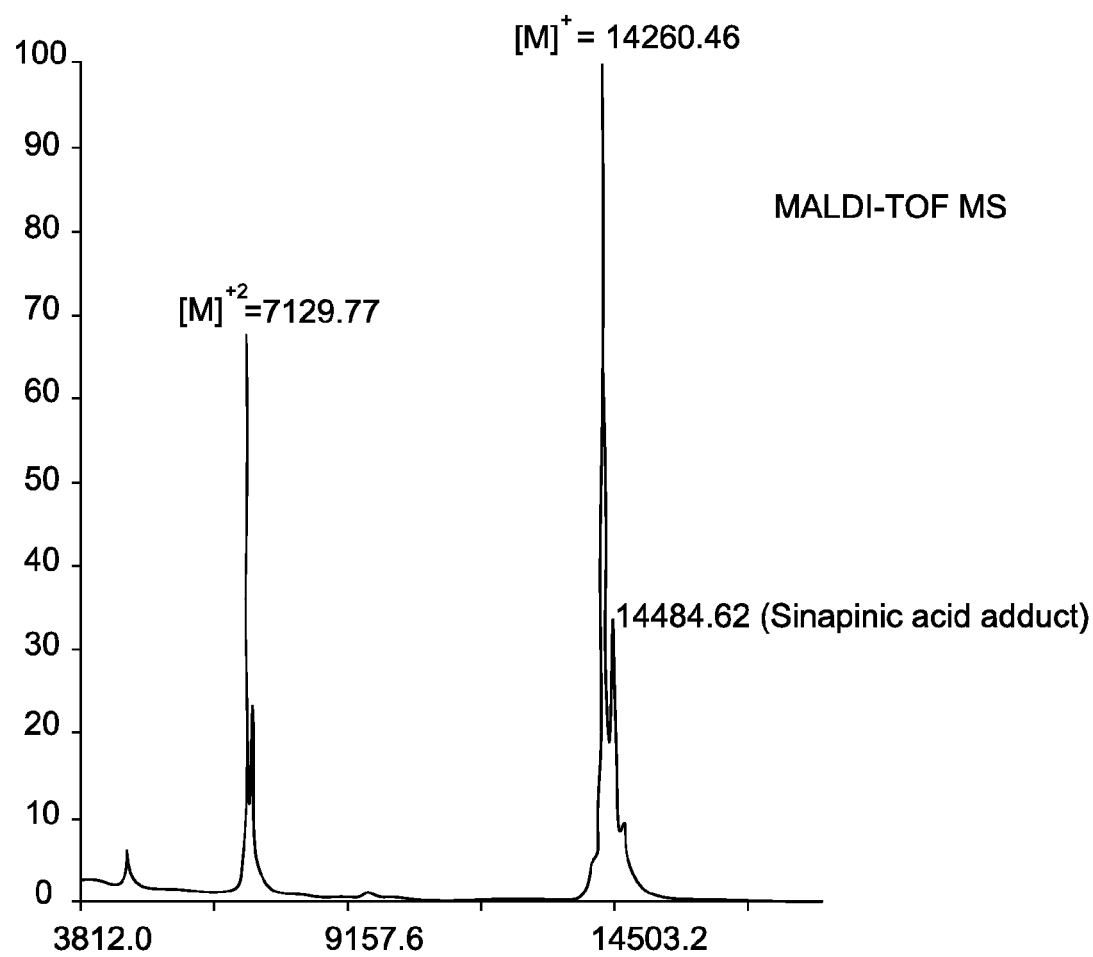
FIG. 4 shows the MALDI-TOF MS data of an alkynylated affibody (22).

Anti-Her2 affibody, 14 kDa (1 mg as a lyophilized powder) was dissolved in 460 μL of phosphate buffered saline (PBS). The pH of the solution was maintained at 7.4. To this solution was added 40 μL of a 0.5 M solution of dithiothreitol (DTT) dissolved in PBS; the pH was maintained at 7.4. The resulting mixture was stirred at room temperature for 2 h. The reduced affibody was purified via gel filtration. To this pure fraction of reduced affibody was added a 12 μL aliquot of a solution of the Mal-alkyne Bifunctional Linker (1) (0.15 M in DMSO). This reaction mixture was incubated at room temperature for 2 h with moderate stirring. The reaction mixture was purified using gel filtration followed by Centrifugal Ultrafiltration (Amicon), MWCO 5 kDa (Millipore) to obtain purified Alkynylated affibody (22). Characterization of the resulting purified Alkynylated affibody (22) was achieved using (MALDI-TOF-MS) and HPLC followed by LC(ESI)-MS. Yield (%): 78; MS: (MH⁺ calculated: 14260. found: 14260) FIG. 4 shows the MALDI-TOF MS data of Alkynylated affibody (22).

Standard conditions for HPLC analysis of Alkynylated affibody (22): Grace Vydac Protein C4 column was used for HPLC analysis. Solvent A: 100% H₂O, 0.1% TFA, Solvent B: 100% MeCN, 0.1% TFA; detection: UV 216 and 280 nm; flow rate: 1 mL/min. The solvent concentration was changed with time as shown in Table 1 below.

TABLE 1

| Time | % A | % B |
|---|---|---|
| 0 | 100 | 0 |
| 4 | 80 | 20 |
| 16 | 40 | 60 |
| 20 | 0 | 100 |

The typical elution time for the Alkynylated affibody (22) was approximately 11 minutes.

Example 7

Triazole Formation on Bioconjugate Under Cold Conditions

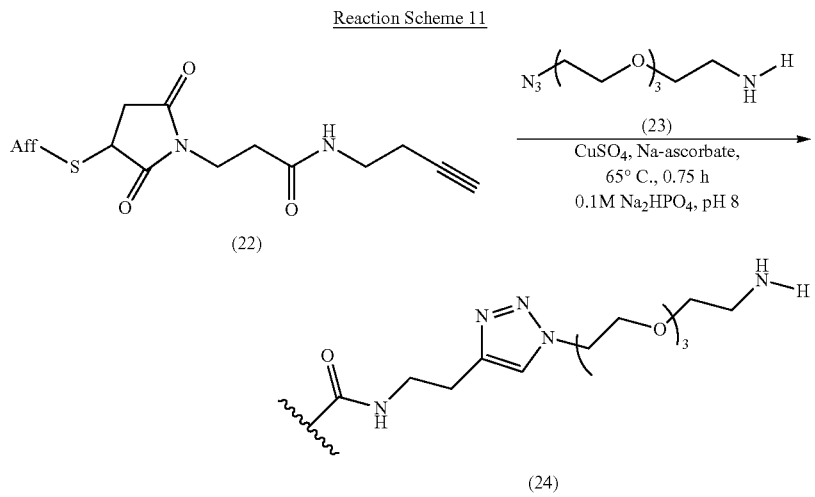

Labeling of Alkynylated-affibody (22) using Azido-PEG (23). To 36 μL of an aqueous solution of sodium phosphate (100 mM, pH 8) was added a 3 μL aliquot of a stock of Alkynylated affibody (22) solution (0.6 mM, ~8 mg/mL in phosphate buffered saline, at pH 7.4). To this solution 1 μL aliquot of a freshly prepared 18 mM solution of 11-Azido-3,6,9-trioxaundecan-1-amine (Azido-PEG) (23) (diluted in 100 mM sodium phosphate, at pH 8) was added. To this solution was then added a 5 μL aliquot of a freshly prepared 10 mM (2 mg/mL) solution of sodium ascorbate (in 100 mM sodium phosphate, pH 8). Finally, a 5 μL aliquot of a freshly prepared 10 mM (1.6 mg/mL) suspension of copper (II) sulfate (in 100 mM sodium phosphate, pH 8) was added to the reaction mixture. These additions thus yielded the following final concentrations for reagents and substrate-Alkynylated affibody (22) (36 μM), the Azido PEG (23) (360 μM), sodium ascorbate (1 mM), and CuSO4 (1 mM).

The resulting solution was mixed at 65° C. with moderate agitation for 0.75 h. The reaction mixture was then immediately diluted to 4 mL in pure water (MilliQ) and concentrated to <100 μL using an Amicon Centrifugal Ultrafiltration unit, MWCO 5 kDa (Millipore). This water dilution-concentration sequence was repeated two additional times in order to remove excess reagents. Characterization of the resulting purified conjugate (24) was achieved using MALDI-TOF-MS and High Performance Liquid Chromatography followed by LC(ESI)-MS. Yield (%): 42. MS: (MH+ calculated: 14478. found: 14492).

freshly prepared 10 mM (1.6 mg/mL) suspension of copper (II) sulfate (in 100 mM sodium phosphate, pH 8) was added to the reaction mixture. These additions yielded the following final concentrations for reagents and substrate: Alkynylated affibody (22) (36 μM), Cy5-labeled azido-PEG (25a) (360 μM), sodium ascorbate (1 mM), and CuSO4 (1 mM).

The resulting solution was mixed at 65° C. with moderate agitation for 0.75 hours. The reaction mixture was then immediately diluted to 4 mL in pure water (MilliQ) and concentrated to <100 μL using an Amicon Centrifugal Ultrafiltration unit, MWCO 5 kDa (Millipore). This water dilution-concentration sequence was repeated two additional times in order to remove excess reagents. Characterization of the resulting Example 8

Labeling of Alkynylated-Affibody (22) Using Cy5-Labeled Azido PEG (25a)

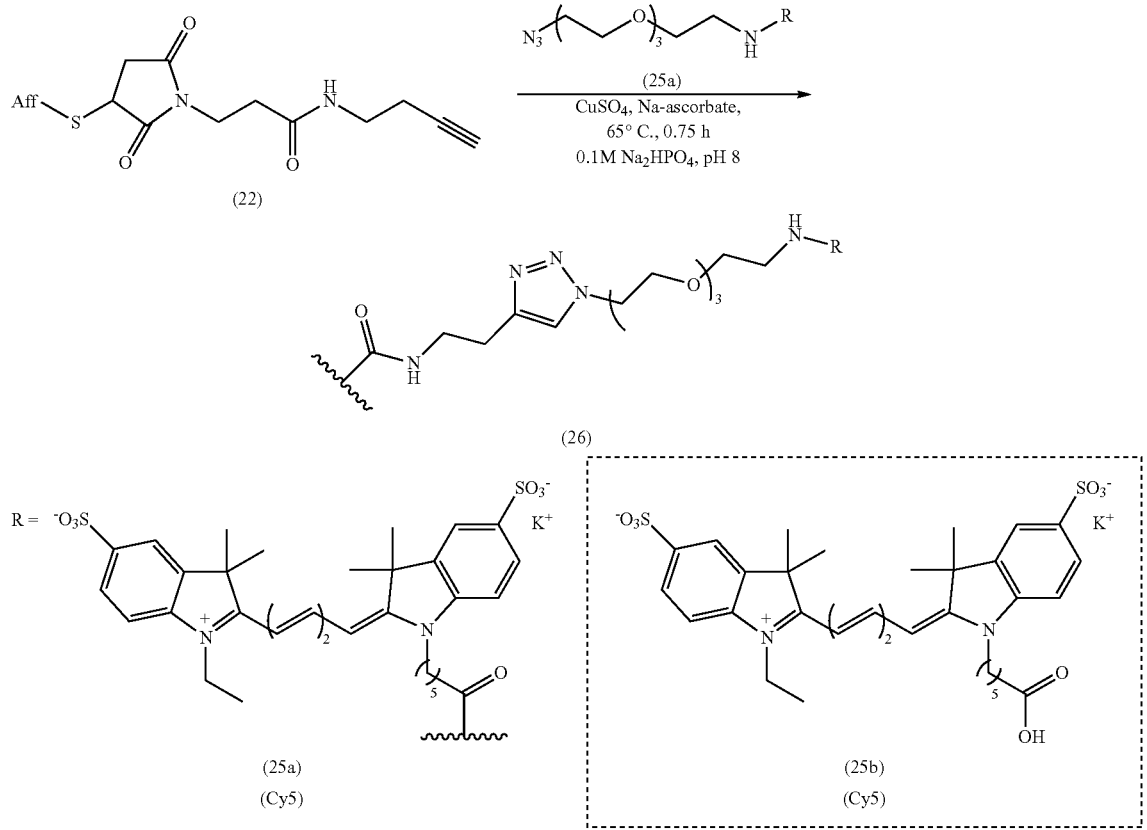

To 36 μL of an aqueous solution of sodium phosphate (100 mM, pH 8) was added a 3 μL aliquot of a stock of Alkynylated affibody (22) solution (0.6 mM, ~8 mg/mL in phosphate buffered saline, pH 7.4). Next was added a 1 μL aliquot of a freshly prepared 18 mM solution of Cy5-labeled azido-PEG (25a) (diluted in 100 mM sodium phosphate, pH 8). To this solution, a 5 μL aliquot of a freshly prepared 10 mM (2 mg/mL) solution of sodium ascorbate (in 100 mM sodium phosphate, pH 8) was then added. Finally, a 5 μL aliquot of a purified conjugate (26) was achieved by HPLC and SDS-PAGE protein gel monitoring the dye's fluorescence emission (FIG. 5).

Example 9

Triazole Formation on Alkynylated Affibody (22) Under Hot Conditions

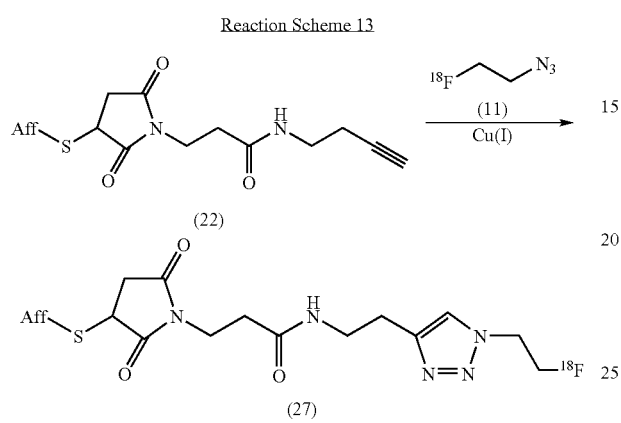

(27)

Labeling of Anti-Her2 affibody (22) with $^{18}$F. An aqueous solution of copper(II) sulfate (5 μL, 0.0249 mg, 0.1 μmol) was mixed with sodium ascorbate (0.198 mg, 1 μmol) in sodium phosphate buffer (5 μL, 100 mM, pH 8.0) and alkynylated affibody (22) (50 μg, 3.57 nmol) in PBS (5 μL). After addition of 2-[$^{18}$F]fluoroethylazide (11) (264 μCi, 9.8 MBq, prepared as described by Glaser, M., and Årstad, E. (2007), "Click labeling' with 2-[$^{18}$F]fluoroethylazide for Positron Emission Tomography. Bioconj. Chem. 18, 989-993, which is incorporated herein by reference]. in MeCN (20 μl), the mixture was heated at 60° C. for 30 min. Labeling with 2-[18F]fluoroethylazide (11) HPLC analysis of the reaction mixture showed a radioactivity peak co-eluting with the affibody (27) UV signal.

Figure 1A:
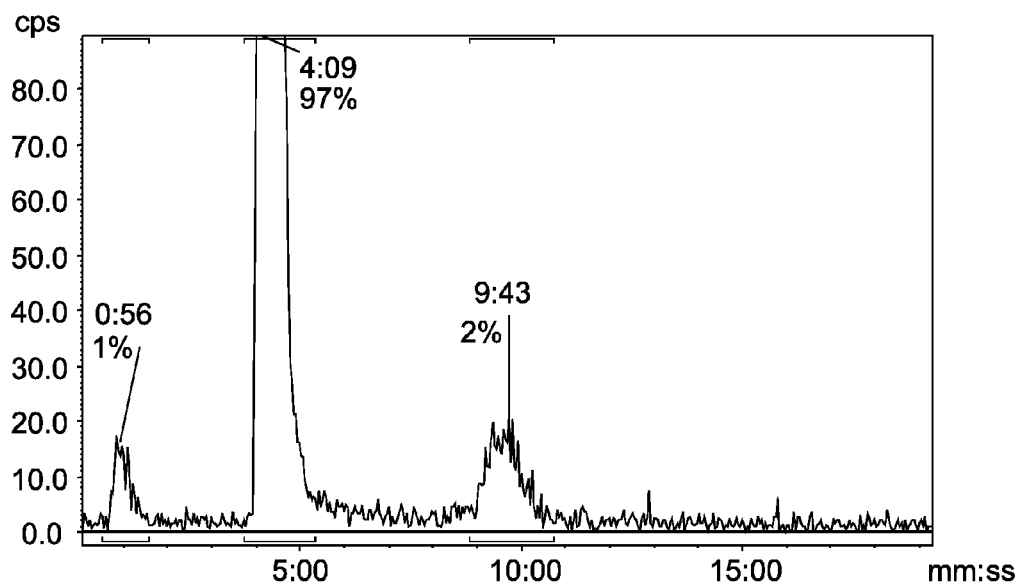
Figure 1B:
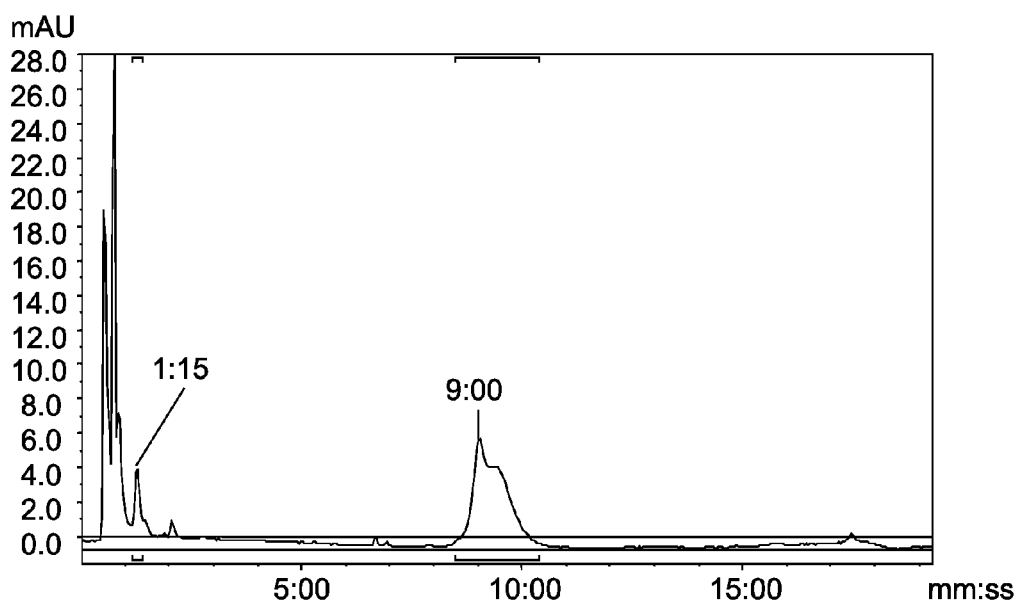

Purification by preparative HPLC (gradient: 5-80% solvent B over 15 min where A=H$_2$O/0.1% TFA and B=MeCN/0.1% TFA, flow rate: 1 mL/min; column: Luna 3 μm C18(2) (Phenomenex), 50×4.6 mm, detection: UV 280 nm. FIG. 1 shows HPLC analysis of a reaction mixture of the non-optimized system showing $^{18}$F click labeled Anti-Her2 affibody (27) (a, radioactivity channel; b, UV channel at 280 nm).

EQUIVALENTS

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. A method for introducing a fluorine atom onto a biomolecule, comprising:
(i) providing a linker including a thiol-reactive terminus and an azido or an alkyne-reactive terminus;
(ii) reacting the thiol-reactive terminus of the linker with the biomolecule including at least one thiol group or a reactive derivative thereof; and
(iii) subsequently reacting the azido or the alkyne-reactive terminus of the linker with a fluorine-substituted azide or alkyne group;
wherein the linker comprises

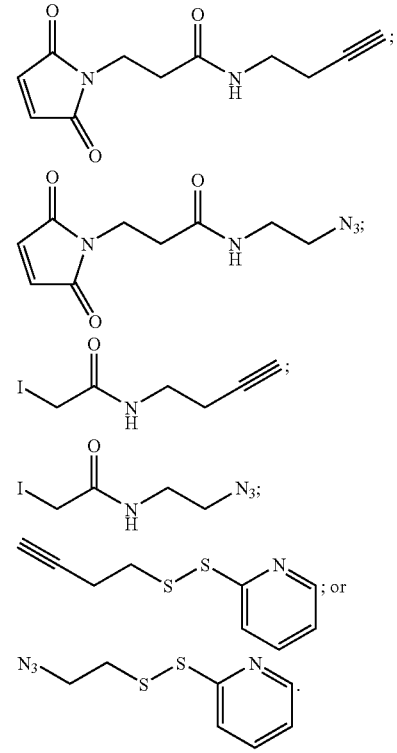

2. The method of claim 1, wherein the biomolecule has more than 50 amino acid residues.
3. The method of claim 2, wherein the biomolecule is an affibody.
4. The method of claim 1, wherein the thiol-reactive terminus is selected from a maleimido group, a haloaliphatic group, a haloaromatic group, a halocycloaliphatic group, a (haloacetyl)alkyl group, a (haloacetyl)cycloalkyl group, a (haloacetyl)aryl group, a vinyl sulfone group, an acryloyl group, an epoxy group, an aziridine group, and a disulfide group capable of a thiol exchange reaction with a thiol group.
5. The method of claim 1, wherein the at least one thiol group includes a cysteine residue or a thiol-containing non-natural amino acid.
6. The method of claim 1, wherein the thiol-reactive terminus of the linker is a maleimido group.
7. The method of claim 1, wherein the reactive derivative of the biomolecule is produced by treating the biomolecule with a reducing agent.
8. The method of claim 1, wherein the linker is produced by a method comprising reacting an amine compound with a carboxylic acid or an activated ester compound to form the linker; wherein the amine compound includes an azido or an alkyne-reactive functional group and the carboxylic acid or the activated ester compound includes a thiol-reactive functional group.
9. The method of claim 1, wherein the fluorine-substituted azide or alkyne comprises a $^{18}$F substituted azide or alkyne or a $^{19}$F substituted azide or alkyne.

10. A bioconjugate comprising structural units derived from:
(i) a biomolecule comprising at least one thiol group; and
(ii) a linker;
wherein the linker is selected from the group consisting of
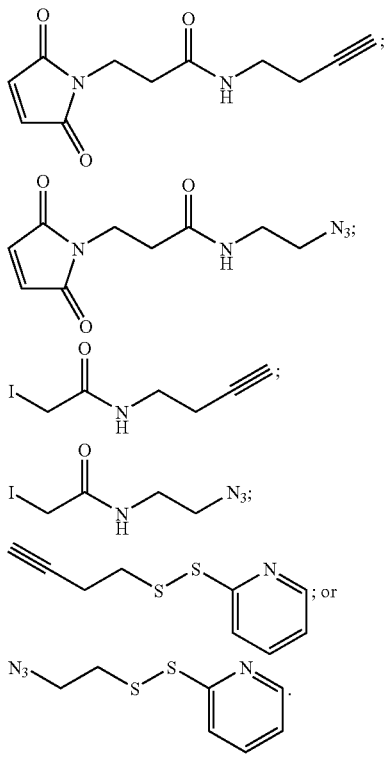
11. The bioconjugate of claim 10, wherein the biomolecule is an affibody.
12. A fluorinated biomolecule made using the method of claim 1.
13. A linker selected from a group consisting of
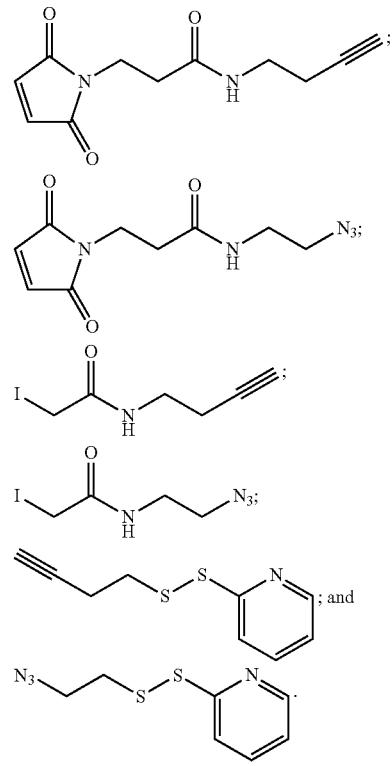
* * * * *